United States Patent [19]

Gibson

[11] Patent Number: 5,114,625
[45] Date of Patent: May 19, 1992

[54] FRAGRANCE DISPENSER FOR EVAPORATING AROMATIC LIQUID

[76] Inventor: Clyde W. Gibson, 423 Lakeview Dr., Harrisburg, N.C. 28075

[21] Appl. No.: 658,187

[22] Filed: Feb. 20, 1991

[51] Int. Cl.⁵ .............................................. B01F 3/04
[52] U.S. Cl. .............................. 261/30; 261/DIG. 65; 261/62; 261/96; 261/99; 261/102; 261/72.1; 422/124
[58] Field of Search ............... 261/30, DIG. 65, 62, 261/96, 99, 102, 72.1; 422/124; 98/30

[56] References Cited

U.S. PATENT DOCUMENTS

| | | |
|---|---|---|
| 1,911,871 | 5/1933 | Andersen . |
| 1,962,100 | 6/1934 | Bryan ................................. 261/104 |
| 2,152,466 | 3/1939 | Clyne .................................. 261/99 |
| 2,323,721 | 7/1943 | McLindon .......................... 261/62 |
| 2,608,436 | 8/1952 | Baughman . |
| 2,678,810 | 5/1954 | Chandler ............................. 261/92 |
| 2,776,166 | 1/1957 | Mendelson . |
| 2,786,714 | 3/1957 | Saleny ................................. 261/99 |
| 2,828,953 | 4/1958 | Hartmann . |
| 2,867,866 | 1/1959 | Steele ........................... 261/DIG. 65 |
| 3,211,380 | 10/1965 | Skerritt ................................ 98/30 |
| 3,298,674 | 1/1967 | Gilbertson .................... 261/DIG. 65 |
| 3,336,734 | 8/1967 | Schultz ............................... 261/96 |
| 3,442,197 | 5/1969 | Cobarg ............................... 98/30 |
| 3,540,445 | 11/1970 | Moyat ................................ 261/99 |
| 3,633,881 | 1/1972 | Yurdin . |
| 3,747,902 | 7/1973 | Bailey . |
| 3,757,494 | 9/1973 | Keuls .................................. 261/99 |
| 3,836,129 | 9/1974 | Perelmutr et al. ................... 261/102 |
| 3,923,934 | 12/1975 | Watkins ............................. 261/102 |
| 4,059,422 | 11/1977 | Steiner ........................ 261/DIG. 65 |
| 4,064,203 | 12/1977 | Cox . |
| 4,067,692 | 1/1978 | Farris ............................ 261/DIG. 65 |
| 4,173,604 | 11/1979 | Dimacopoulos . |
| 4,370,300 | 1/1983 | Mori et al. .......................... 261/96 |
| 4,500,480 | 2/1985 | Cambio, Jr. ....................... 261/72.1 |
| 4,722,264 | 2/1988 | DeGuisseppe ..................... 261/30 |

Primary Examiner—Tim Miles
Attorney, Agent, or Firm—Bell, Seltzer, Park & Gibson

[57] ABSTRACT

A fragrance dispenser for circulating air and evaporating an aromatic fluid into the air is disclosed. The fragrance dispenser include a wick holder body having a fluid reservoir and a wick receiving passage. The passage communicates with the fluid reservoir and includes an exposed wick receiving passage and channel portion. A wick is disposed in the wick receiving channel and has a fluid receiving end disposed in the reservoir for drawing liquid therefrom into the wick and an exposed portion positioned in the exposed portion of the wick receiving channel. A fan housing is connected to the wick holder body and includes a fan for blowing air over the exposed portion of the wick. A wick cover, supported by the wick holder body, is movable between a substantially closed position covering the exposed portion of the wick and an open position where the wick is exposed to the flow of air provided by the fan. A sleeve and linkage mechanism connects the wick cover for moving the wick cover from a substantially closed position and a preselected open position for selectively limiting the amount of air which flows over the exposed portion of the wick and controlling the amount of fluid evaporated from the wick.

16 Claims, 7 Drawing Sheets

FRAGRANCE DISPENSER FOR EVAPORATING AROMATIC LIQUID

FIELD OF THE INVENTION

This invention relates to a fragrance dispenser for circulating air and evaporating an aromatic fluid into the air without generating heat, dust, mist, or residue.

BACKGROUND OF THE INVENTION

Air fresheners and fragrance dispensers are used in the home, automobile and other closed environments for "freshening" the air and providing a pleasing scent to the environment. Many different prior art air fresheners and fragrance dispensers have been designed for use in combination with a furnace or other large and bulky air handling systems. For example, U.S. Pat. No. 2,786,714 to Saleny discloses a home air freshener having a sleeve mounted to a furnace wall, and a tube with a wick contained therein slidable in the sleeve. The wick is connected to a source of fragrance producing liquid. The furnace air is drawn over the tube and wick for producing a fragrance which is distributed throughout the environment supplied by the furnace by means of the furnace air. This type of air freshener has been found undesirable because it only operates in combination with a furnace or other larger air handling device.

Other prior art air freshener and fragrance dispenser designs include units having self contained fans for recirculating air and evaporating a fragrance liquid which typically is drawn on a wick. Typical examples of this type of air freshener and fragrance dispenser include the inventions disclosed in the U.S. Pat. Nos. 1,911,871, 2,068,518, 2,828,953, 3,633,881, and 4,064,203. Many of these types of prior art devices do not provide any means for diverting a controlled flow of air against the wick or for limiting exposure of the wick to the flow of air and thus limiting the amount of fluid evaporated from the wick. Also in many of these prior art devices, only the end of the wick is exposed. It is more desirable to expose a portion of the longitudinal length of the wick material rather than only an end portion as in some of the prior art devices.

SUMMARY OF THE INVENTION

The fragrance dispenser in accordance with the present invention overcomes many of the disadvantages of the above prior art by having the wick disposed in a wick receiving channel and providing means for blowing the air over the exposed portion of the wick. One end of the wick is disposed in a fluid reservoir which advantageously is a constant level reservoir for drawing the liquid therefrom. A wick cover is movable between a substantially closed position covering the exposed portion of the wick and an extended, open position where the wick is fully exposed to the flow of air. Means is operatively connected to the wick cover for moving the wick cover from the substantially closed position into preselected open positions between said closed and extended, open positions for selectively limiting the amount of air which flows over the wick and controlling the amount of fluid evaporated from the wick.

In the preferred embodiment, the fragrance dispenser includes a wick holder body. An air passage extends upward through the wick holder body and has a lower air inlet opening and an upper circular air outlet opening. A wick receiving passage communicates with the fluid reservoir and extends through the body and outward along the upper edge of the circular outlet opening to form an exposed annular channel portion adjacent the outlet opening.

A wick is disposed longitudinally in the wick receiving passage and channel and has a fluid receiving end disposed in the reservoir for drawing fluid therefrom into the wick. Means is mounted to the wick holder body below the inlet opening for forcing air upward through the air channel and over the exposed portion of the wick held within the annular channel. The air movement means advantageously comprises a fan housing mounted under the wick holder body. A fan is supported by the fan housing and blows air upward through the air passageway.

An annular wick cover is supported by the wick holder body and is dimensioned for substantially covering the annular channel and wick contained therein. The wick cover is movable between a closed position covering the exposed portion of the wick and an extended raised position where the wick is exposed to a flow of air upwardly forced through the air passageway. Means supported by the wick cover body is operatively connected to the wick cover for raising the wick cover into preselected raised positions between the closed position and the extended, open position for selectively limiting the amount of air which flows over the exposed wick whereby the amount of fluid evaporation can be controlled.

A circular air deflection baffle is positioned above the circular air outlet opening for deflecting air laterally across the outlet opening when air is forced upward through the air passageway. The circular air deflection baffle is dimensioned for engaging the interior peripheral edge of the annular wick cover as the wick cover is raised into the extended raised position closing the air passage for forming an enlarged deflection surface for deflecting air completely over the exposed portion of the wick.

A support shaft is mounted to the wick holder body and extends upward through the air passageway. The air deflection baffle is connected to the support shaft. A sleeve is mounted on the shaft and is movable vertically on the shaft. The wick cover is connected to the sleeve. A linkage mechanism interconnects the sleeve and a cam. The cam has notches for engaging the linkage so that as the cam is rotated, the linkage engages a notch for raising the wick cover a preselected amount above the exposed portion of the wick received in the wick receiving channel.

In a second embodiment, the wick holding body includes a support member having the fluid reservoir contained therein. A concave member extends from the support member. The wick receiving channel extends in the concave member and into the support member. The wick is disposed longitudinally in the concave member so that a portion of the wick length is exposed. A second concave member is slidably mounted on the first concave member for selectively covering the exposed portion of the wick.

DESCRIPTION OF THE DRAWINGS

The advantages of the present invention having been stated, other advantages will become apparent in association with the following drawings in which.

DETAILED DESCRIPTION

Figure 1:
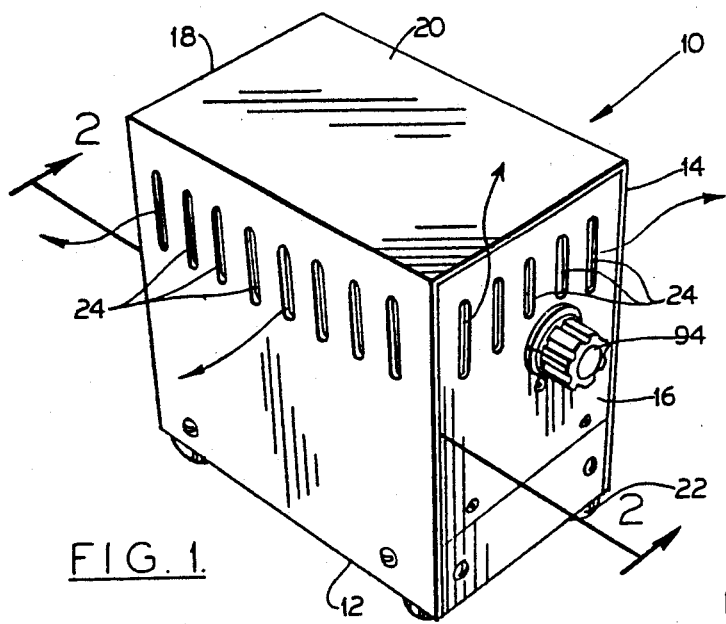
FIG. 1 is an isometric view of the fragrance dispenser in accordance with the first preferred embodiment of the present invention.

Referring now to the drawings, and more particularly to FIGS. 1 through 10, there is disclosed a first preferred embodiment of the fragrance dispenser, illustrated generally at 10, in accordance with the present invention. As shown in FIG. 1, the fragrance dispenser 1c is a compact, self contained unit which can be placed in a convenient location in a room or other closed environment for circulating air and evaporating an aromatic fluid into the air for "perfuming" and "freshening" the air circulated through the fragrance dispenser. The fragrance dispenser 10 includes an outer housing body having bottom 12, side 14, front 16, rear 18, and top 20 walls. Rubber grommets 22 are positioned at each corner on the bottom wall 12 to provide legs for supporting the fragrance dispenser 10 and to provide air intake from underneath. The upper portions of front 16, rear 18, and side 14 walls contain air diffusion slots 24 for allowing scented air to be discharged from the fragrance dispenser 10.

Figure 3:
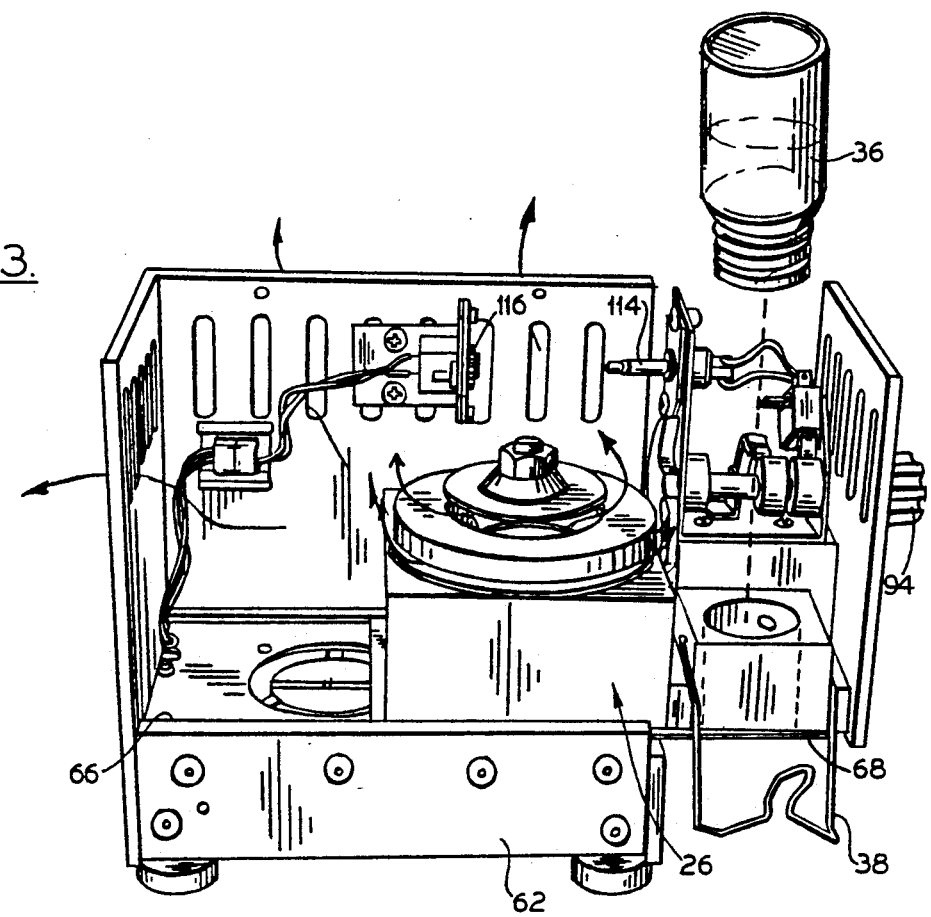
FIG. 3 is an isometric view of the fragrance dispenser in accordance with the first preferred embodiment of the invention and showing a side housing body wall and top cover removed from the fragrance dispenser and wick holder body disconnected and partially removed with the fan exposed.
Figure 5:
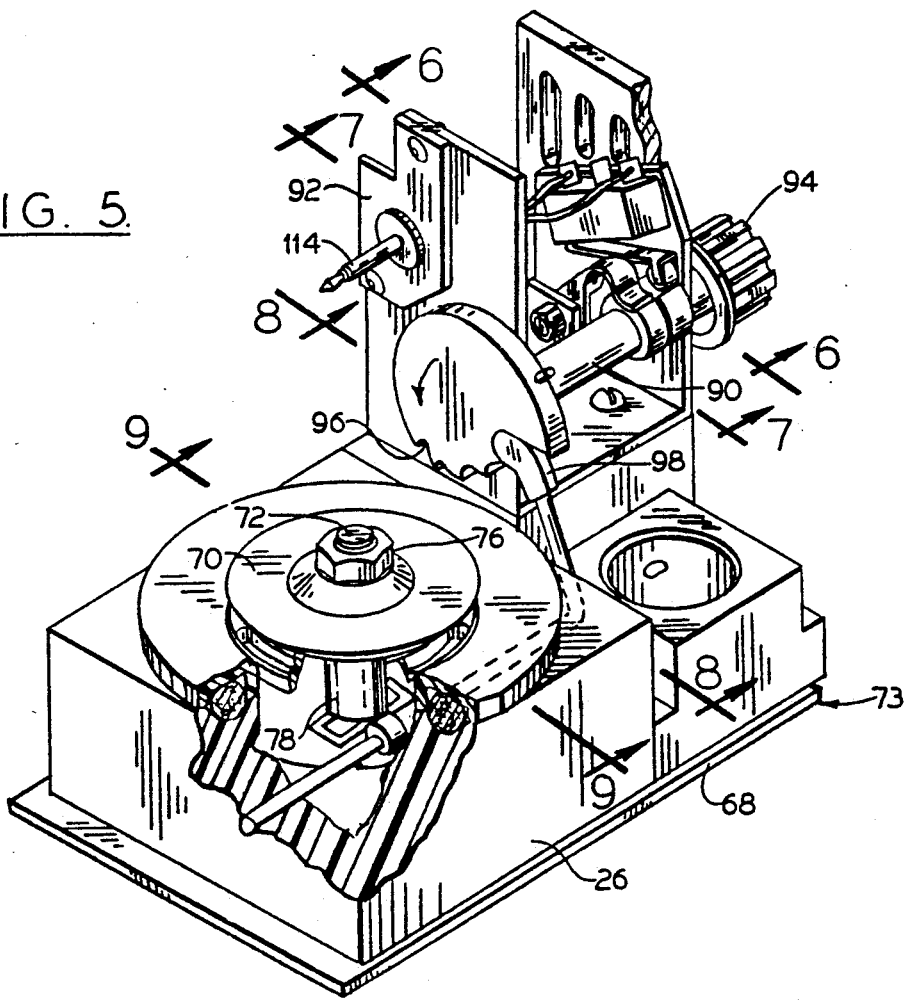
FIG. 5 is an isometric view of the wick holder body and other associated components of the fragrance dispenser mounted on the wick holder body.
Figure 6:
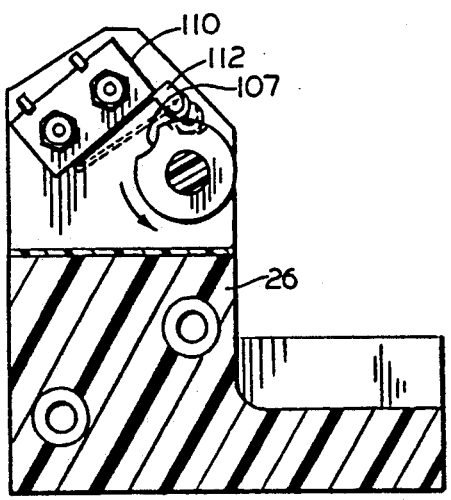
FIG. 6 is a sectional view taken along line 6—6 of FIG. 5.
Figure 10:
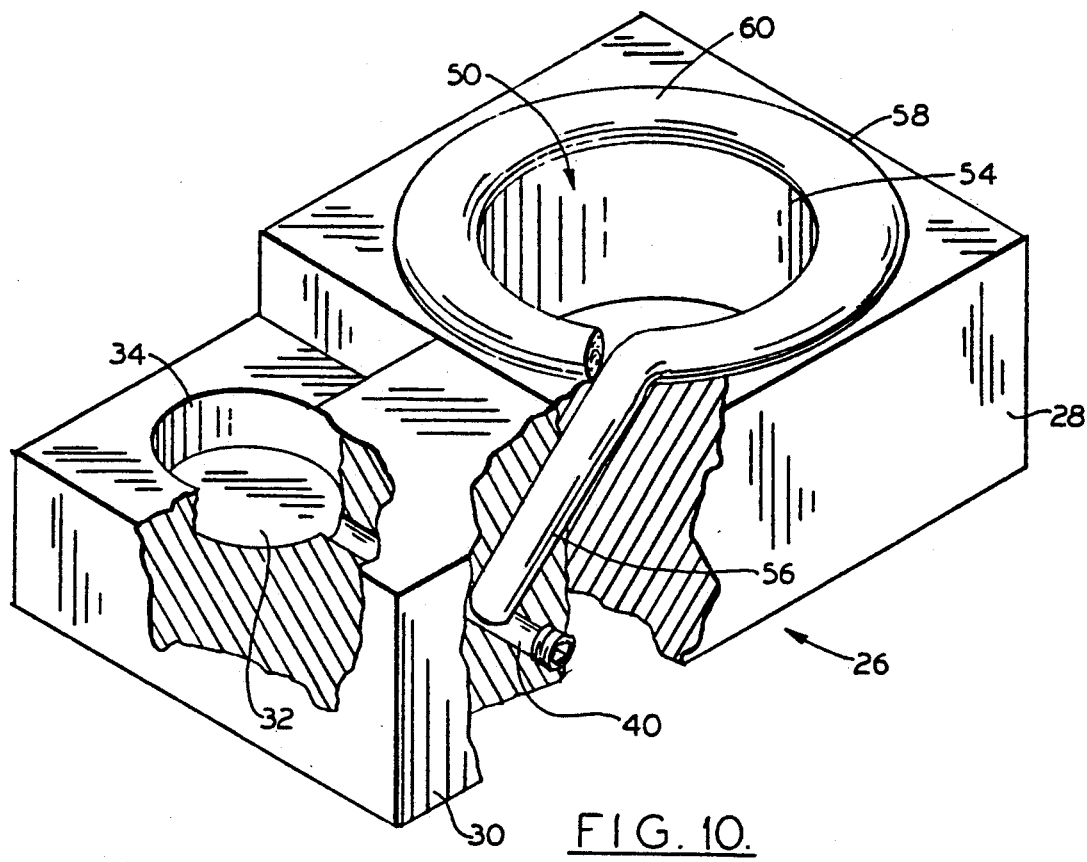
FIG. 10 is an isometric view of the wick holder body and showing the wick contained within the wick receiving channel and passage.
Figure 11:
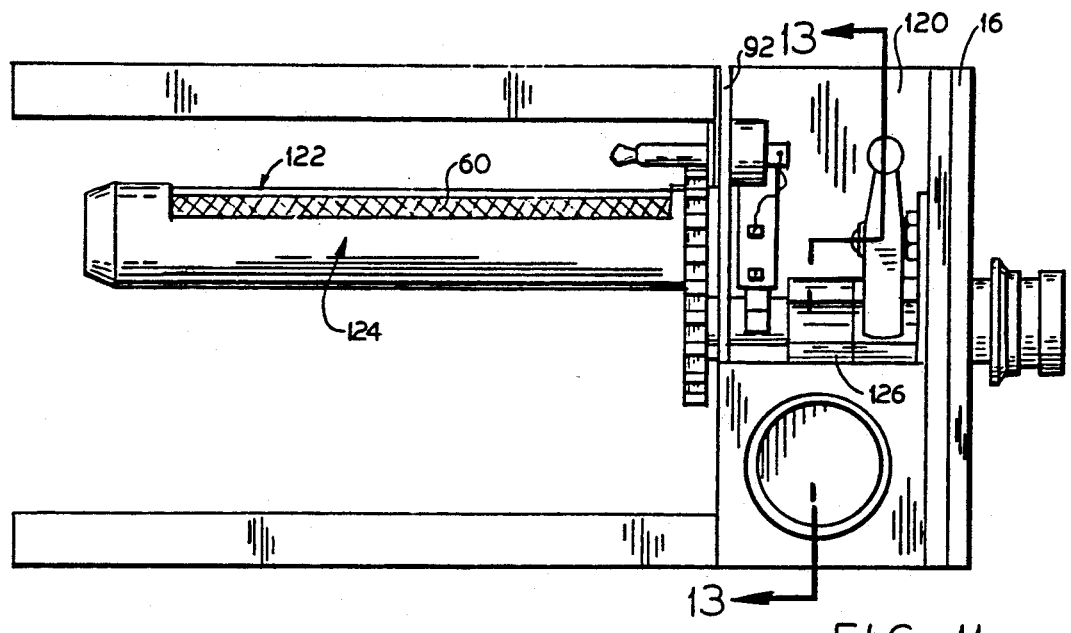
FIG. 11 is a schematic illustration of a wick holder body in accordance with a second embodiment of the present invention.
Figure 12:
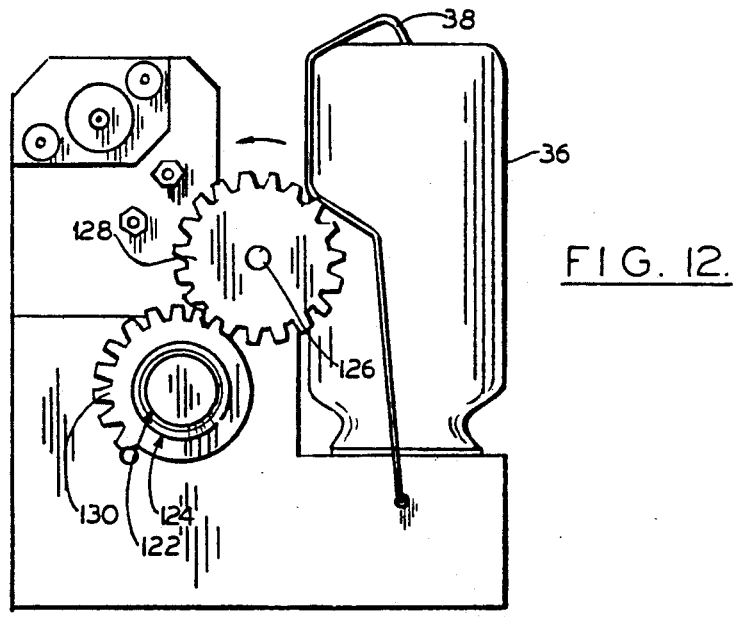
FIG. 12 is a schematic, side elevation view of the fragrance dispenser in accordance with the second embodiment of the present invention.
Figure 13:
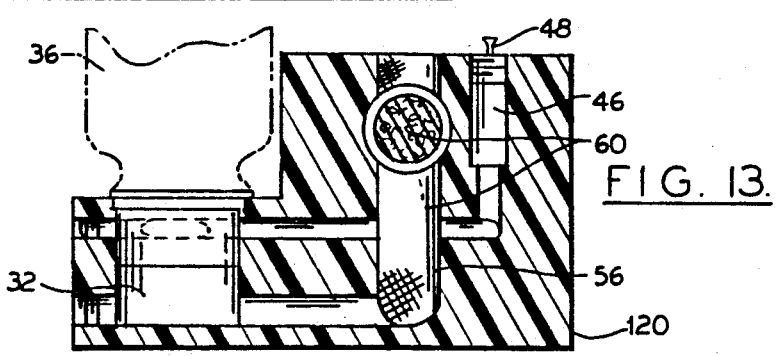
FIG. 13 is a sectional view taken along line 13—13 of FIG. 11.

As disclosed in FIGS. 3, 5 and 10, the fragrance dispenser 10 includes a main wick holder body 26 formed of a suitable material such as aluminum or a strong, rigid plastic. When the wick holder body 26 is formed out of plastic, cost of production can be decreased because the body can be formed by conventional injection molding techniques.

Figure 2:
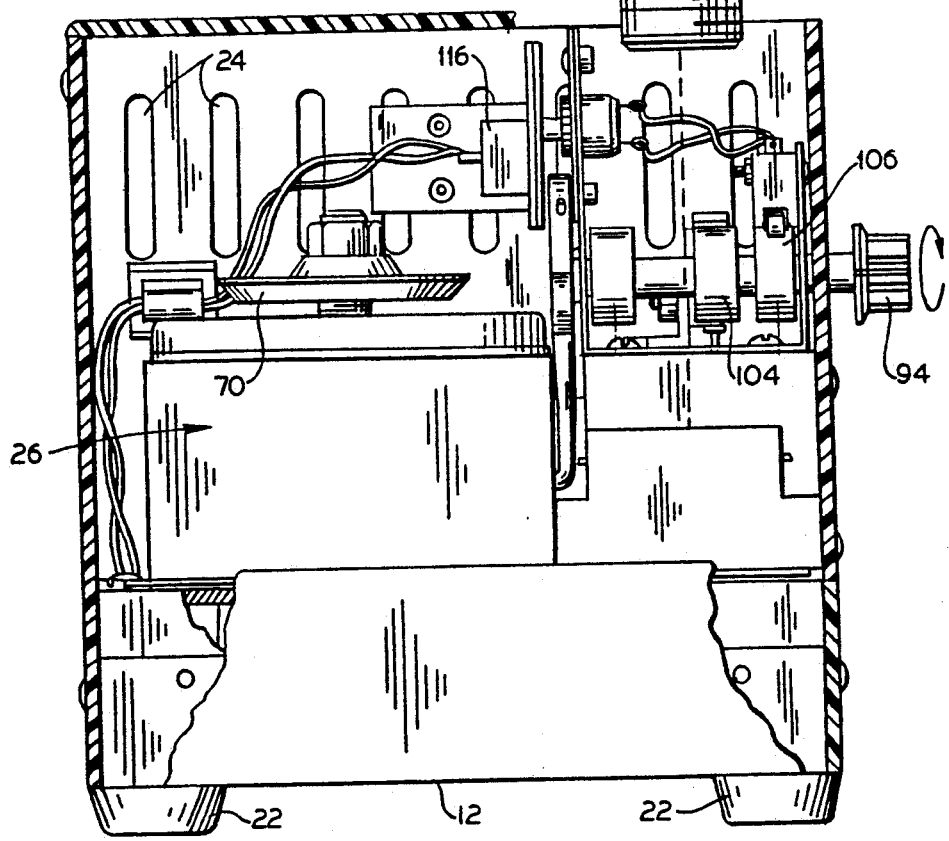
FIG. 2 is a sectional view taken along line 2—2 of FIG. 1 and showing the basic working components of the fragrance dispenser.

The wick holder body 26 is substantially rectangular configured and includes a first larger wick holder portion 28 and a second, smaller reservoir portion 30 (FIG. 10). The smaller reservoir portion 30 includes a fluid reservoir 32 for holding an aromatic fluid therein. The wick holder body 26 includes a reservoir opening 34 which is dimensioned for receiving an inverted bottle 36 containing an aromatic fluid therein (FIG. 2). The inverted bottle 36 forms an air-tight seal for controlling atmospheric pressure and preventing fluid loss if the fragrance dispenser is accidentally knocked over. A retaining clip 38 holds the bottle in place.

A horizontally extending passage 40 extends through the smaller reservoir portion 30 of the wick holder body 26 and has an access opening in the side of the wick holder body 26. An allen screw 44 is inserted into the passage access opening for preventing the aromatic fluid from flowing out from the fluid reservoir 32. The use of an allen screw 44 and access opening is advantageous because the fluid reservoir can be emptied if the scent and type of liquid is changed. When desirable, the wick holder body assembly 26 can be removed by sliding out, as will be described later in detail. The retaining clip 38 can be loosened, and the bottle 36 removed. The allen screw 44 is removed and the old wick is removed and the reservoir and connecting passages are cleaned from any remaining former scented fluid. The unit is reassembled with new wick 60, and a new bottle containing a fluid of different scent is installed.

The fluid reservoir 32 forms a sealed cavity, and includes an upper opening communicating with the fluid reservoir 32. A vent valve 46 is positioned in the opening and vents the fluid reservoir 32 when the fragrance dispenser 10 is in use. The vent valve 46 is similar to an auto tire valve having a central shaft 48 which allows air flow therethrough when the central shaft 48 is pushed. The valve vents the reservoir to the atmosphere during operation of the fragrance dispenser 10. The venting is necessary for permitting withdrawal of the aromatic fluid from the reservoir.

Figure 9A:
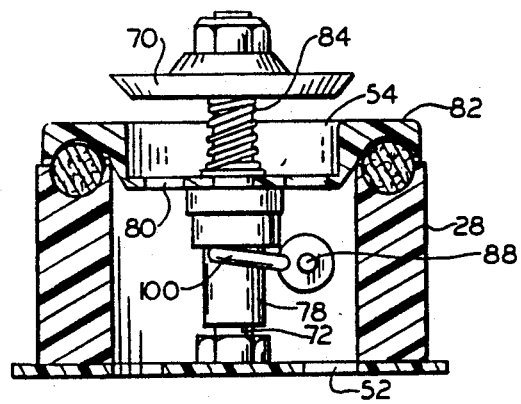
FIGS. 9A through 9C are corresponding sectionals taken along line 9—9 of FIG. 5 and showing the positional relationship of the wick cover relative to the wick holder body for preselected positions of the cam in FIGS. 8A through 8C.
Figure 9B:
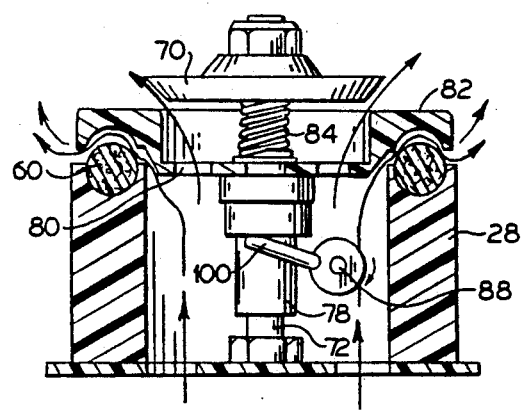
Figure 9C:
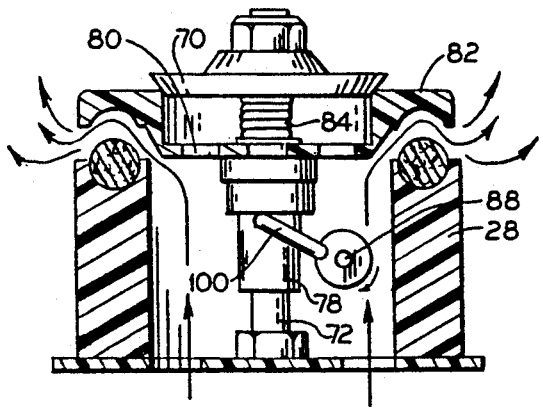

As illustrated in FIG. 10, a circular air passageway 50 extends upward through the first larger portion 28 of wick holder body 26 and includes a lower air inlet opening 52 and upper circular air outlet opening 54. A wick receiving passage 56 extends upward through the wick holder body 26 and has one end communicating with the fluid reservoir 32 (FIG. 10) and extends outward from the wick holder body 26 and along the upper peripheral edge of the circular air outlet opening 54 to form an exposed annular channel portion 58 adjacent the outlet opening (FIGS. 9A through 9C). A wick 60 is longitudinally disposed in the wick receiving passage 56 and channel. The wick 60 includes a fluid receiving end extending downward through the passage 56 into the fluid reservoir 32 for drawing fluid therefrom into the wick. As illustrated, the portion of the wick 60 received in the annular channel 58 is exposed for allowing air contact and evaporation of the fluid contained in the wick 60.

Means is positioned below the inlet opening 54 of the air passageway 50 for forcing air upward through the passageway and over the exposed portion of the wick 60. The annular configuration of the wick receiving channel 58 provides a high surface area of wick 60 contact with air forced upward through the air passageway 50. In the preferred embodiment, the blowing means advantageously is a fan housing 62 mounted below the wick holder body 26 such as illustrated in FIG. 3 and which includes a fan 64 mounted to the housing. The fan housing 62 is substantially rectangular configured and is dimensioned along its length and width similar to the overall length and width dimensions of the wick holder body 26. In the preferred embodiment, the fan housing includes sliding channels 66 in which tongue extensions 68 on the wick holder body 26 can be received so that the wick holder body 26 can be slid into a secured position over the fan housing 62. Sliding engagement of the wick holder body 26 and fan housing 62 is advantageous to facilitate separation of both units.

Figure 4:
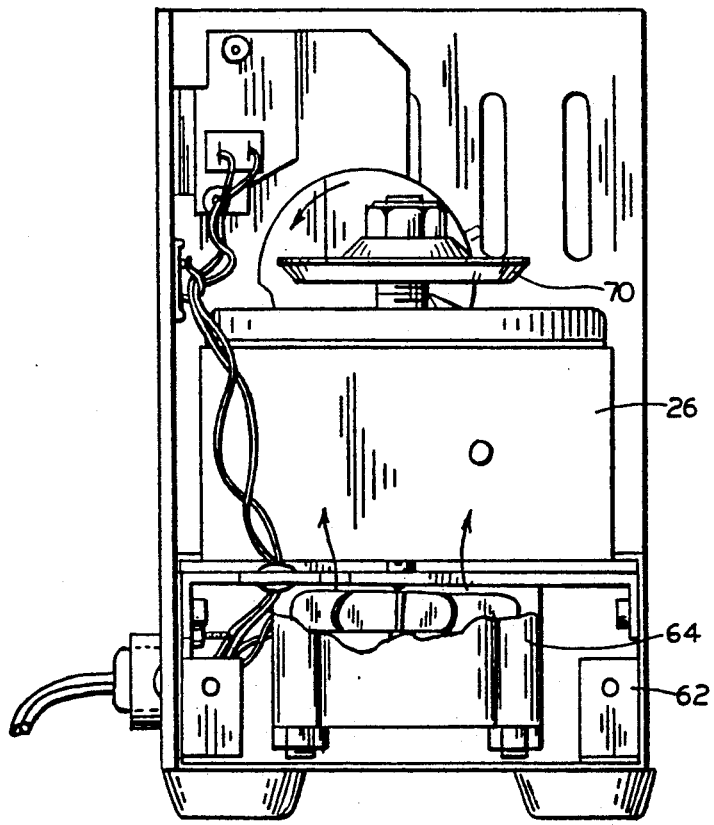
FIG. 4 is an end view of the fragrance dispenser and showing the positional relationship of the fan and wick holder body.

The fan housing 62 includes a central opening which is aligned with the air passageway 50 of the wick holder body 26 when both the wick holder body 26 and fan housing 62 are positioned together (FIG. 4). The fan 64 is mounted to the fan housing opening for drawing air from the bottom and into the air passageway 50 of the wick holder body 26. The fan 64 is a d.c. operated fan which is typical of this type of fan used in smaller applications. However, other fans can be used if desired. Additionally, other means, such as a low pressure air source of a natural air movement can be utilized for blowing air up the air passageway 50 thus allowing the fragrance dispenser to be added to air movement systems such as heating, cooling and other ventilation systems. A fan is desired, however, because it is better adapted to be self contained as a unit with the fragrance dispenser 10. During operation, the air forced upward through the air passageway 50 is directed across the exposed portion of the wick 60 and the aromatic, fragrance fluid contained in the wick 60 is evaporated into the air to provide a pleasing scent.

An air deflection baffle 70 is positioned above the air outlet opening 54 to aid in deflecting air laterally across the opening and over the exposed portion of the wick 60 to allow an increased efficiency in evaporation of the aromatic fluid. The air deflection baffle 70 is supported on a central support shaft 72 extending downward through the wick holder body 26 opening. Inward extending legs 74 which preferably are mounted on a body support plate 73 integrally connected to the wick holder body and positioned at the air inlet opening 52 support the shaft 72 in a vertical orientation. The flanges 62 advantageously are an integral part of the body support plate 73. The upper portion of the shaft 72 is threaded and the circular air deflection baffle 70 is received thereon and engages a shoulder (not shown) to maintain the baffle in a predetermined vertical height above the outlet opening. A nut 76 is threaded on the end of the support shaft 72 to retain the baffle to the shaft 72.

A sleeve 78 is received over the shaft 72 and is movable in a range of vertical positions as illustrated in FIGS. 9A through 9C. Legs 80 extend outward from the upper portion of the sleeve 78 and interconnect to an annular wick cover 82 which is dimensioned for covering the annular wick receiving channel 56 and wick 60 contained therein. The annular wick cover 82 is movable between a closed position where the wick 60 is covered and an extended, raised position where the wick 60 is fully uncovered, for allowing evaporation of the aromatic fluid. The wick cover is movable also into preselected raised positions between the closed and extended raised positions for selectively limiting the amount of air which flows over the exposed portion of the wick 60 and limiting the amount of fluid evaporated from the wick 60. A spring 84 is positioned between the circular air deflection baffle 70 and the support legs 80 of the annular wick cover 82 and applies a biasing force against the wick cover 82 and into a downward closed position.

Figure 8A:
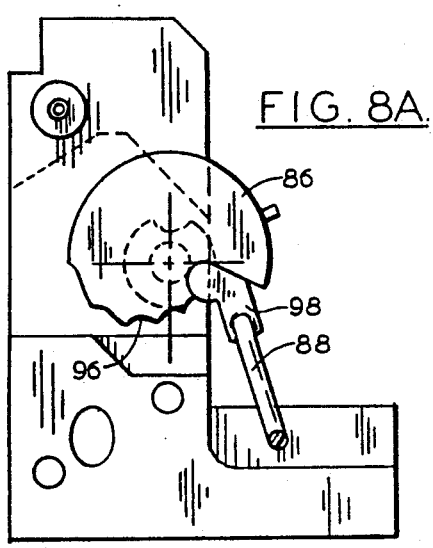
FIGS. 8A through 8C are sectionals taken along line 8—8 of FIG. 5 and showing the positional relationship of the cam and linkage mechanism connected to the sleeve and wick cover.
Figure 8B:
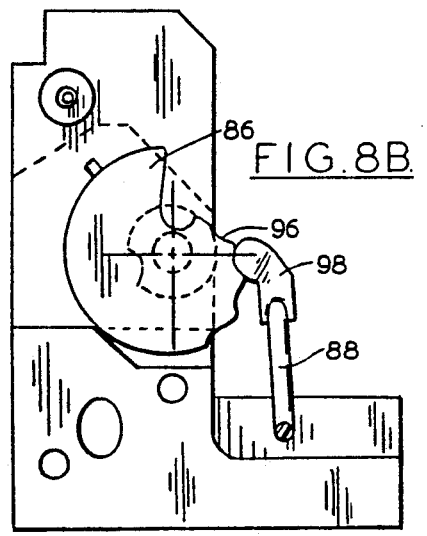
Figure 8C:
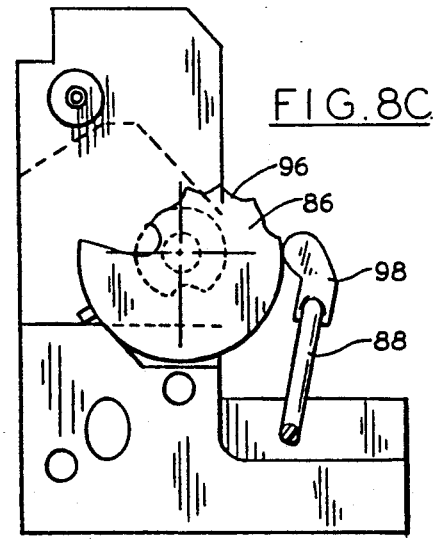

In accordance with the present invention, means is provided for moving the annular wick cover 82 between closed and extended, raised positions and into the preselected raised positions. As illustrated in FIGS. 5, 8 and 9, a cam 86, and a linkage 88 interconnecting the cam 86 and sleeve 78, provide the desired mechanism for raising the annular wick cover 82 from off the annular receiving channel 58. A cam support shaft 90 extends through the front wall 16 of the fragrance dispenser 10 and through an interior support wall 92. The cam 86 is positioned at the end of the shaft 90 (FIG. 5). A control knob 94 is positioned on the shaft end outside the front wall 16. The cam surface includes a plurality of notches 96. The linkage 88 extends through the wick holder body 26 and includes a first end having a cam follower 98 for engaging the notches 96 of the cam surface (FIGS. 8A through 8C). The other end of the linkage 88 extends through the wick holder body 26 and into the air passageway 50. A bracket arm 100 is attached to the end of the linkage 88 and engages an upper shoulder 102 positioned on the sleeve 78 (FIGS. 9A through 9C).

When the shaft 90 is rotated and the cam 86 is turned, the linkage 88 is moved forcing the bracket arm 100 against the shoulder 102 to raise the sleeve 78. The cam follower 98 fits into each of the successive notches 96 as the cam 86 is turned corresponding to selected raised positions of the wick cover 82. The notches 96 are spaced in a generally increasing radius from the center of the cam 86 to provide successive raised positions for the wick cover. In the illustrated embodiment, six notches 96 corresponding to six wick cover positions are illustrated. Three of those raised positions are illustrated in FIGS. 9a through 9c. As the cam 86 is rotated so that the cam follower 98 engages notches 96 of increasing radius from the center, the wick cover 82 is raised.

Figure 7:
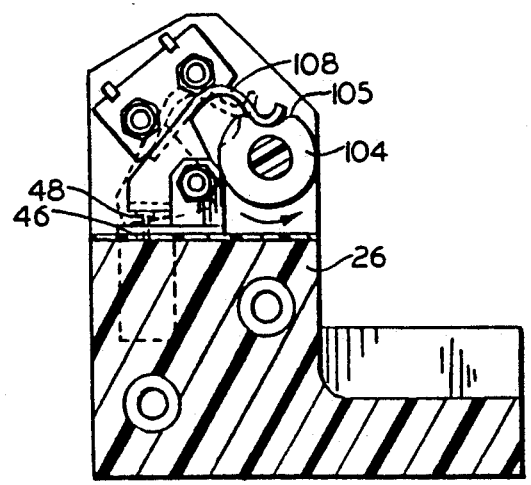
FIG. 7 is a sectional view line taken along line 7—7 of FIG. 5.

The cam support shaft 90 includes two circular lobes 104, 106 positioned between the interior support wall 92 and front wall 16 of the fragrance dispenser 10. The first circular lobe 104 adjacent the support wall 92 includes a notch 105 (FIG. 7). A rocker arm 108 is connected to the interior of the front wall 16 and includes a first end which rides on the lobe and a second end engaging the central shaft 48 of the vent valve 46 of the fluid reservoir 32. When the cam support shaft 90 is oriented so that the wick cover 82 is lowered over the wick receiving channel 58 in an off position, the rocker arm 108 is positioned in the notch 105 on the lobe and tension is released from the central shaft of the vent valve 46. When the shaft 90 is turned, raising the wick cover 82 off the wick receiving channel 58, one end of the rocker arm 108 is raised thus pushing the other end of the rocker arm 108 downward into engagement with the central shaft of the vent valve 98 allowing atmospheric pressure to advantageously maintain a preferred constant level reservoir thereby maintaining a constant degree of wick saturation in the annular wick receiving channel. When this is accomplished the wick 60 then can draw liquid upward into the portion of the wick exposed in the annular wick receiving channel.

The second circular lobe 106 adjacent to the interior support wall 92 is dimensioned similar to the first circular lobe 104 and also includes a notch 107 oriented with the notch 105 of the first lobe. A microswitch 110 is positioned on the interior of the front wall 16 and includes a contact arm 112 which engages the surface of the second lobe 106. The microswitch 110 has an on-off capability and is connected to the fan 64 to operate the on-off control for the fan 64. When the cam support shaft 90 is turned and wick cover raised, the contact arm 112 moves out from the notch 107 (FIG. 6) and closes the microswitch 110 for operating the fan 64.

The fragrance dispenser 10 can be adapted for use with electrical current compatible with fan motor 64. The transformer with cord used for reducing household current to 6 or 12 volts d.c. needed to operate the fan 64 would be located at the outlet or the transformer may be built inside the fragrance dispenser and plugged directly into a wall receptacle. The system includes a low voltage plug 114 on the support wall 92 which engages an enclosed jack 116 supported on the side wall 14. The plug and jack 114, 116 engage each other when the wick holder body 26 is slid into position over the fan housing 62 (FIG. 3). These types of connectors commonly are found in conventional consumer electronic products.

To operate the fragrance dispenser 10 in accordance with the first preferred embodiment of the present invention, the control knob 94 is turned slightly, thus moving the microswitch arm 112 and rocker arm 108 out of engagement of the lobe notches 105, 107. The microswitch 110 is closed thus activating the fan 64 which forces air upward through the air passageway 50. The upward moving air engages the air deflection baffle 70 and is deflected laterally across the top of the wick cover 82 (FIG. 9B) and partially over the exposed wick 60. Additionally, the rocker arm 108 is moved and pushes the central shaft of the vent valve 46 downward thus allowing venting of the fluid reservoir 32 so that the fluid is drawn upward into the wick 60. As the control knob 94 is rotated through its range of positions, the wick cover 82 is raised off from the wick receiving channel 58. The amount of air flow over the wick 60, and, hence, the amount of evaporation of aromatic fluid from the wick 60 is controlled by the vertical position of the wick cover 82. The wick cover 82 is positioned by rotating the control knob 94 to a predetermined position to where the cam follower 98 engages a preselected notch 96 on the cam surface. At the intermediate position illustrated in FIG. 9B, air is forced upward over the exposed portion of the wick 60 and also between the air deflection baffle 70 and the top portion of the annular wick cover 82. Thus the amount of evaporation is limited. In a fully raised position illustrated in FIG. 9C, the top portion of the wick cover 82 engages the air deflection baffle 70 and all air forced upward through the air passageway 50 is directed over the exposed portion of the wick 60. In this raised wick cover 82 position, a greater amount of aromatic fluid is evaporated from the wick causing a greater amount of scent to be distributed into the environment.

Referring now to FIGS. 11 through 14, there is illustrated a second embodiment of the fragrance dispenser 10. In the second embodiment, the wick holder support member 120 contains the fluid reservoir 32. A concave member 122 in the form of a half-tube member extends from the support member 120 and the wick is received in the concave member 122. The wick 60 extends through the concave member 122 and downward through the support member 120 and into the fluid reservoir 32. The fluid reservoir 32 is similar in structure to the fluid reservoir 32 of the first embodiment and includes a vent valve 46 as noted before. A second concave member 124 in the form of a half-tube member 124 is slidably received onto the first concave member 122 and is movable in an arcuate path relative to the fixed first concave member 122. The second concave member 124 is movable from a position received about the first concave member 122 and a position where the second concave member 124 covers the exposed wick 60. A rotatable spur gear support shaft 126 extends through a front wall 16 of the fragrance dispenser 10 and the support wall 92. A first spur gear 128 is positioned on the end of the support shaft 126 and engages a second spur gear 130 which is attached to the second concave member 124. As the support shaft 126 is rotated, the second concave member 124 is rotated relative to the first fixed concave member 122.

Figure 14:
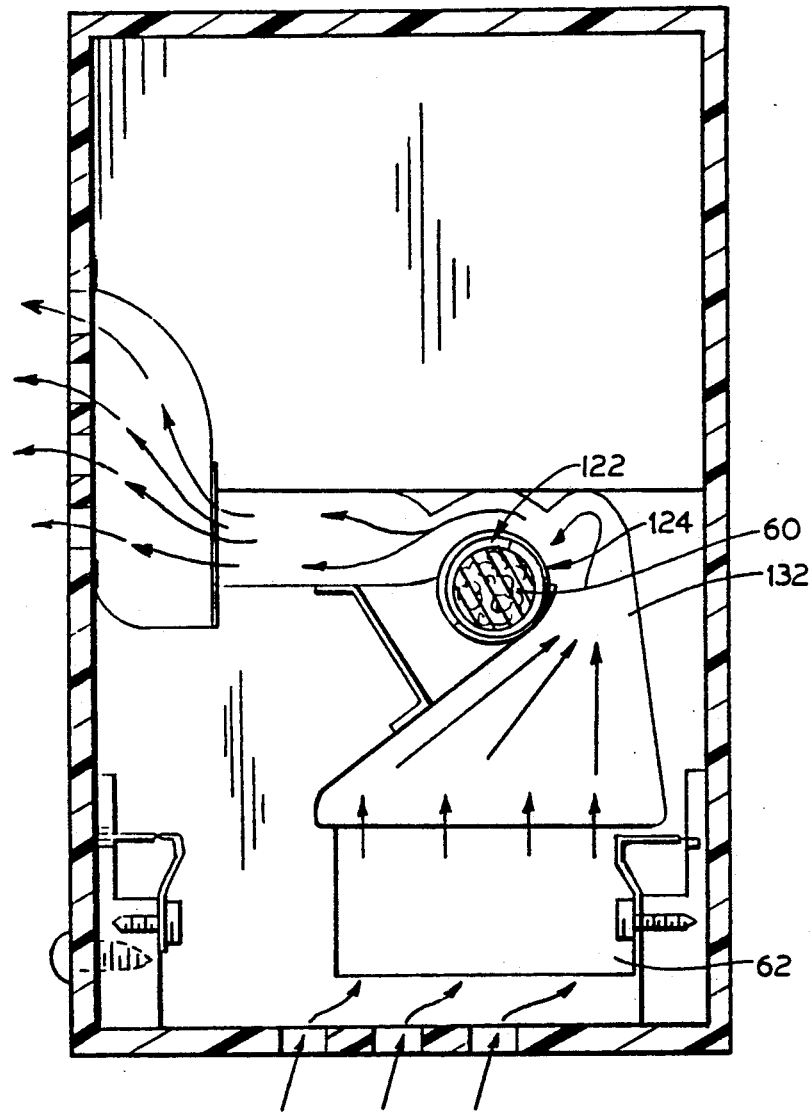
FIG. 14 is a side elevation view of the fragrance dispenser in accordance with the second embodiment of the present invention and showing the positional relationship of the fan housing and wick holder body.

The fan housing 62 is positioned at the bottom of the fragrance dispenser frame body and includes a vertical extending deflection baffle 132 as illustrated in FIG. 14 for moving air produced by a fan upward into the fan housing and into engagement with the exposed portion of the wick.

The construction of the half-tube concave interengaging support members 122, 124 is well adapted for use in both modular fragrance dispenser units as illustrated, and for use in air duct work where the half-tube concave members have the wick 60 contained therein can be placed in the duct work of a furnace or air conditioning system.

In the drawings and specification, there have been disclosed typical preferred embodiments in the invention and, although specific terms are employed, they are used in a generic and descriptive sense only, and not for purposes of limitation, the scope of the invention being set forth in the following claims.

That which is claimed is:

1. A fragrance dispenser for circulating air and evaporating an aromatic liquid into the air comprising
   a wick holder body having a fluid reservoir for holding an aromatic fluid and the like, and a wick receiving passage, said passage communicating with said fluid reservoir and having an exposed wick receiving channel portion, and wherein said wick holder body includes an air passageway extending therethrough and having an air inlet opening and circular air outlet opening, said exposed portion of said wick receiving channel extending adjacent the peripheral edge of said circular outlet opening,
   a wick longitudinally positioned in said wick receiving passage and being exposed along the wick length received in the channel, said wick having a fluid receiving end disposed in said reservoir for drawing fluid therefrom into said wick,
   a fan housing mounted to said wick holder body, and a fan mounted to said fan housing for blowing air through said housing and over said exposed wick portion,
   a wick cover supported by said wick holder body and movable between a substantially closed position covering the exposed portion of the wick and an extended open position where the wick is fully exposed to a flow of air produced by the fan, and means operatively connected to said wick cover for moving the wick cover from the substantially closed position into preselected open positions between said closed and extended, open positions for selectively limiting the amount of air which flows over the exposed portion of the wick and controlling the amount of fluid evaporated from the wick.

2. A fragrance dispenser according to claim 1, wherein said fan housing body is connected to said wick holder body adjacent to said inlet opening for blowing air through said air passageway and over said exposed portion of said wick.

3. A fragrance dispenser according to claim 1, including means supported by said wick holding body for deflecting air flow produced by said blowing means onto said wick.

4. A fragrance dispenser according to claim 1, including a valve communicating with said fluid reservoir for venting the fluid reservoir to the atmosphere.

5. A fragrance dispenser for evaporating an aromatic liquid into the air comprising
   a wick holder body having a fluid reservoir for holding an aromatic fluid and the like, and a wick receiving passage, said passage communicating with said fluid reservoir and having an exposed wick receiving channel portion, and wherein said holding body comprises a support member having said reservoir contained therein, a concave member extending from support member, said wick receiving channel extending in said concave member so that a portion of said wick length is exposed and a second concave member slidably mounted on said concave member for selectively covering the exposed portion said wick,
   a wick longitudinally positioned in said wick receiving passage and being exposed along the wick length received in the channel, said wick having a fluid receiving end disposed in said reservoir for drawing fluid therefrom into said wick,
   means mounted to said wick holder body for blowing air over said wick portion,
   wherein said second concave member is movable between a substantially closed position covering the exposed portion of the wick and an extended open position where the wick is fully exposed to a flow of air produced by the fan, and
   means operatively connected to said second concave member for moving the second concave member from the substantially closed position into preselected open positions between said closed and extended, positions for selectively limiting the amount of air which flows over the exposed portion of the wick and controlling the fluid evaporated from the wick.

6. A fragrance dispenser for circulating air and evaporating an aromatic liquid into the air comprising
   a wick holder body having a fluid reservoir, an air passageway extending upward through said wick holder body and having a lower air inlet opening and an upper circular air outlet opening, and a wick receiving passage communicating with said fluid reservoir, said wick receiving passage extending from said fluid reservoir, through said body and along the upper peripheral edge of said circular outlet opening to form an exposed annular wick receiving channel portion adjacent the outlet opening,
   a wick positioned in said wick receiving passage and channel and being exposed along the wick length received in the channel and having a fluid receiving end disposed in said reservoir for drawing fluid therefrom into said wick,
   means mounted to said wick holding body below said inlet opening for forcing air upwardly through said air channel and over the exposed portion of the wick held within the annular wick receiving channel,
   an annular wick cover supported by the wick holder body and movable between a substantially closed position covering the annular channel and the exposed portion of the wick, and an extended, raised position where the wick is exposed to a flow of air forced upwardly through the air passageway.

7. A fragrance dispenser according to claim 6 including means operatively connected to said wick cover for raising said wick cover off from said annular wick holding channel into preselected raised positions between said closed and extended positions for selectively limiting the amount of air which flows over the exposed portion of the wick and controlling the amount of fluid evaporated from the wick.

8. A fragrance dispenser according to claim 6, wherein said wick holder body includes an opening communicating with said fluid reservoir and dimensioned for receiving an inverted fluid holding bottle and forming an air tight seal between the bottle and wick holder body.

9. A fragrance dispenser according to claim 6, wherein said wick holder body includes a valve communicating with said fluid reservoir for venting the fluid reservoir to the atmosphere.

10. A fragrance dispenser according to claim 9 including means operatively connected to said valve means for opening said valve means when said wick cover is raised.

11. A fragrance dispenser according to claim 6, including a circular air deflection baffle positioned above the circular air outlet opening for deflecting air laterally across the outlet opening.

12. A fragrance dispenser according to claim 11, wherein said circular air deflection baffle is dimensioned for engaging the interior peripheral edge of said annular wick cover as said wick cover is raised to said extended raised position for deflecting air under the air deflection baffle and the wick cover and over the exposed portion of the wick held within the annular wick receiving channel.

13. A fragrance dispenser according to claim 11, including a support shaft mounted to said wick holding body and extending upward through said air channel, said air deflection baffle being mounted on said support shaft.

14. A fragrance dispenser according to claim 13, wherein said means operatively connected to said wick cover for raising said wick cover off from said annular wick receiving channel into preselected raised positions includes a sleeve slidably mounted on said shaft, means interconnecting said sleeve to said annular configured wick cover, and means for raising said sleeve on said shaft for raising said wick cover into said predetermined raised positions.

15. A fragrance dispenser according to claim 14, wherein said means for raising said sleeve includes a rotatable cam and linkage means operatively connected to said cam and sleeve for selectively raising said sleeve to said predetermined positions as said cam is rotated.

16. A fragrance dispenser according to claim 15, including control means operatively connected to said cam for turning said fan off and on as said cam is rotated a preselected amount.

* * * * *

UNITED STATES PATENT AND TRADEMARK OFFICE
CERTIFICATE OF CORRECTION

PATENT NO. : 5,114,625

DATED : May 19, 1992

INVENTOR(S) : Clyde W. Gibson

It is certified that error appears in the above-identified patent and that said Letters Patent is hereby corrected as shown below:

Column 3, line 55, "1c" should be -- 10 --.

Column 5, line 52, the numeral "62" should be -- 68 --.

Column 6, line 66, the numeral "98" should be -- 46 --.

Column 6, line 68, after "level" insert -- in the --.

Signed and Sealed this

Twentieth Day of July, 1993

Attest:

MICHAEL K. KIRK

Attesting Officer

Acting Commissioner of Patents and Trademarks